US00PP14318P29

(12) United States Plant Patent
Roberson

(10) Patent No.: US PP14,318 P2
(45) Date of Patent: Nov. 25, 2003

(54) LANTANA PLANT NAMED 'ROBMORNORG'

(50) Latin Name: *Lantana camara*
Varietal Denomination: Rohmornorg

(76) Inventor: Robert J. Roberson, 31706 E. Pink Hill Rd., Grain Valley, MO (US) 64029

( * ) Notice: Subject to any disclaimer, the term of this patent is extended or adjusted under 35 U.S.C. 154(b) by 0 days.

(21) Appl. No.: 10/259,946

(22) Filed: Sep. 29, 2002

(51) Int. Cl.[7] ..... A01H 5/00

(52) U.S. Cl. ..... Plt./227
(58) Field of Search ..... Plt./227

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Lantana plant named 'Robmornorg', characterized by its outwardly spreading, recumbent and mounding plant habit; densely foliated, full and bushy appearance; freely flowering habit; and flowers that are initially yellow, then becoming orange and eventually red in color.

1 Drawing Sheet

Botanical classification/cultivar designation: *Lantana camara* cultivar Robmornorg.

BACKGROUND OF THE INVENTION

The present Invention relates to a new and distinct cultivar of Lantana plant, botanically known as *Lantana camara,* and hereinafter referred to by the cultivar name Robmornorg.

The new Lantana is a product of a planned breeding program conducted by the Inventor in Grain Valley, Mo. The objective of the breeding program is to create freely-flowering and vigorous Lantanas that root easily and do not produce seed.

The new Lantana originated from a self-pollination made by the Inventor during the summer of 1995 of the Lantana cultivar Radiation, not patented. The new Lantana was selected as a single plant from the resulting progeny of the self-pollination by the Inventor in a controlled environment in Grain Valley, Mo.

Asexual reproduction of the new cultivar by terminal cuttings taken in Grain Valley, Mo. since 1995, has shown that the unique features of this new Lantana are stable and reproduced true to type in successive generations.

SUMMARY OF THE INVENTION

Plants of the cultivar Robmornorg have not been observed under all possible environmental conditions. The phenotype may vary somewhat with variations in environment and culture such as temperature, light intensity, daylength, water status, and/or fertilizer rate or type without, however, any variance in genotype.

The following traits have been repeatedly observed and are determined to be the unique characteristics of 'Robmornorg'. These characteristics in combination distinguish 'Robmornorg' as a new and distinct cultivar:

1. Outwardly spreading, recumbent and mounding plant habit.
2. Densely foliated, full and bushy appearance.
3. Freely flowering habit.
4. Flowers that are initially yellow, then becoming orange and eventually red in color.

Plants of the new Lantana are most similar to plants of the parent, the cultivar Radiation. In side-by-side comparisons conducted in Grain Valley, Mo., plants of the new Lantana differed from plants of the cultivar Radiation in the following characteristics:

1. Cuttings of plants of the new Lantana rooted more easily than cuttings of plants of the cultivar Radiation.
2. Plants of the new Lantana grew more vigorously than plants of the cultivar Radiation.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lantana.

The photograph at the top of the sheet comprises a side perspective view of a typical plant of 'Robmornorg' in a container.

The photograph at the bottom of the sheet comprises a close-up view of typical developing inflorescences and the upper and lower surfaces of typical leaves of 'Robmornorg'.

DETAILED BOTANICAL DESCRIPTION

Plants used for the aforementioned photographs and following observations and measurements were grown for about 19 weeks in 15.25-cm containers and were pinched twice. Plants were grown in a polycarbonate-covered greenhouse in Lompoc, Calif. during the spring and summer with day temperatures ranging from 21 to 27° C., night temperatures ranging from 16 to 18° C., and light levels ranging from 4,000 to 9,000 foot-candles.

In the following description, color references are made to The Royal Horticultural Society Colour Chart, 1995 Edition, except where general terms of ordinary dictionary significance are used.

Botanical classification: *Lantana camara* cultivar Robmornorg.

Parentage: Self-pollination of *Lantana camara* cultivar Radiation, not patented.

Propagation:

*Type cutting.*—Terminal cuttings.

*Time to initiate roots, summer.*—About 10 days at 27° C.

*Time to initiate roots, winter.*—About 13 days at 27° C.

*Time to produce a rooted young plant, summer.*—About 37 days at 29° C.

*Time to produce a rooted young plant, winter.*—About 44 days at 24° C.

*Root description.*—Fine, fibrous; initially glaucous white becoming closer to 161D with development.

*Rooting habit.*—Freely branching.

Plant description:

*Form.*—Flowering subshrub; initially upright, then outwardly spreading and mounding; recumbent. Freely branching; two lateral branches potentially forming at every node; pinching enhances lateral branch development.

*Plant height.*—About 20 cm.

*Plant diameter.*—About 72 cm.

*Vigor.*—Vigorous growth habit.

*Lateral branches.*—Length: About 44 cm. Diameter: About 4 mm. Internode length: About 3.75 cm. Aspect: Initially upright, then outwardly bending to about 90° from vertical. Strength: Flexible, but strong. Texture: Sparsely pubescent. Color: Young: 144A. Woody: 165C.

*Foliage description.*—Arrangement: Opposite, simple. Length: About 7.5 cm. Width: About 4.6 cm. Shape: Elliptic. Apex: Broadly acute. Base: Acute. Margin: Serrate. Texture, both surfaces: Coarse, rough, leathery; slightly pubescent. Venation pattern: Pinnate, arcuate. Fragrance: Pungent, herb-like. Color: Young foliage, upper surface: 137A. Young foliage, lower surface: 147B. Mature foliage, upper surface: 147A. Mature foliage, lower surface: 147B. Venation, upper surface: 147C. Venation, lower surface: 147D. Petiole length: About 1.5 cm. Petiole diameter: About 1.5 mm. Petiole color: 147B.

Flower description:

*Flower type and arrangement.*—Small solitary salver-form flowers arranged in axillary umbels; flowers face mostly upward or outward. Umbels orientated about 45° from vertical.

*Quantity of flowers.*—Freely flowering with potentially two inflorescences developing per node. Typically two to four open inflorescences per lateral branch in flower at one time with about 40 to 45 flowers per umbel.

*Natural flowering season.*—Spring until frost in the autumn; flowering continuous during this period.

*Flower longevity on the plant.*—About four to five days. Flowers not persistent.

*Fragrance.*—Faint, spicy.

*Inflorescence diameter.*—About 3.5 cm.

*Inflorescence height.*—About 2 cm.

*Flowers.*—Appearance: Flared trumpet, corolla fused, four-parted; flowers roughly rectangular in shape. Diameter: About 8 mm by 6 mm. Corolla tube length: About 1.5 cm. Corolla tube diameter, at base: About 1 mm.

*Flower buds* (*showing color*).—Length: About 6 mm. Diameter: Apex: About 2.25 mm. Base: About 1 mm. Shape: Elongate, oblong. Color: 28C, becoming closer to 42B with development.

*Corolla.*—Arrangement: Single whorl of four petals, fused into flared trumpet. Petal length from throat: About 3 mm. Petal width: About 3.5 mm. Petal shape: Ovoid. Petal apex: Rounded. Petal margin: Entire. Petal texture: Smooth, velvety. Color: Petal, upper surface, when opening: Initially, 17A to 17C, then becoming closer to 28B towards the margins and 23A towards the throat. Petal, lower surface, when opening: 17C. Petal, upper surface, fully opened: Towards the margins, 33A, towards the throat, 33B to 34A. Petal, lower surface, fully opened: 28C. Throat: 28C. Tube: 26C.

*Calyx.*—Arrangement: One single calyx tube per flower. Calyx length: About 1.5 mm. Calyx width: About 1 mm. Apex: Rounded to broadly acute. Texture: Pubescent. Color, upper and lower surfaces: 144D.

*Peduncles.*—Length: About 3 cm. Diameter: About 1 mm. Angle: About 45° from the stem. Strength: Flexible, but strong. Color: 144A.

*Pedicels.*—Length: Less than 0.5 mm. Diameter: Less than 0.25 mm. Color: Close to 144A.

*Reproductive organs.*—Stamens: Quantity/arrangement: Four per flower, adnate to floral tube. Anther shape: Ovoid. Anther length: Less than 1 mm. Anther color: 20A. Pollen amount: Scarce. Pollen color: 20A. Pistils: Quantity: One per flower. Pistil length: About 6 mm. Stigma shape: Bi-lobed. Stigma color: 145A. Style color: About 3.5 mm. Style color: 145C. Ovary color: 145A.

*Fruit/seed.*—Fruit and seed production has not been observed.

Disease/pest resistance: Plants of the new Lantana have not been noted to be resistant to pathogens or pests common to Lantana under commercial greenhouse conditions.

Weather tolerance: Plants of the new Lantana have been observed to be tolerant to rain, wind and temperatures ranging from 0 to 38°.

It is claimed:

1. A new and distinct cultivar of Lantana plant named 'Robmornorg', as illustrated and described.

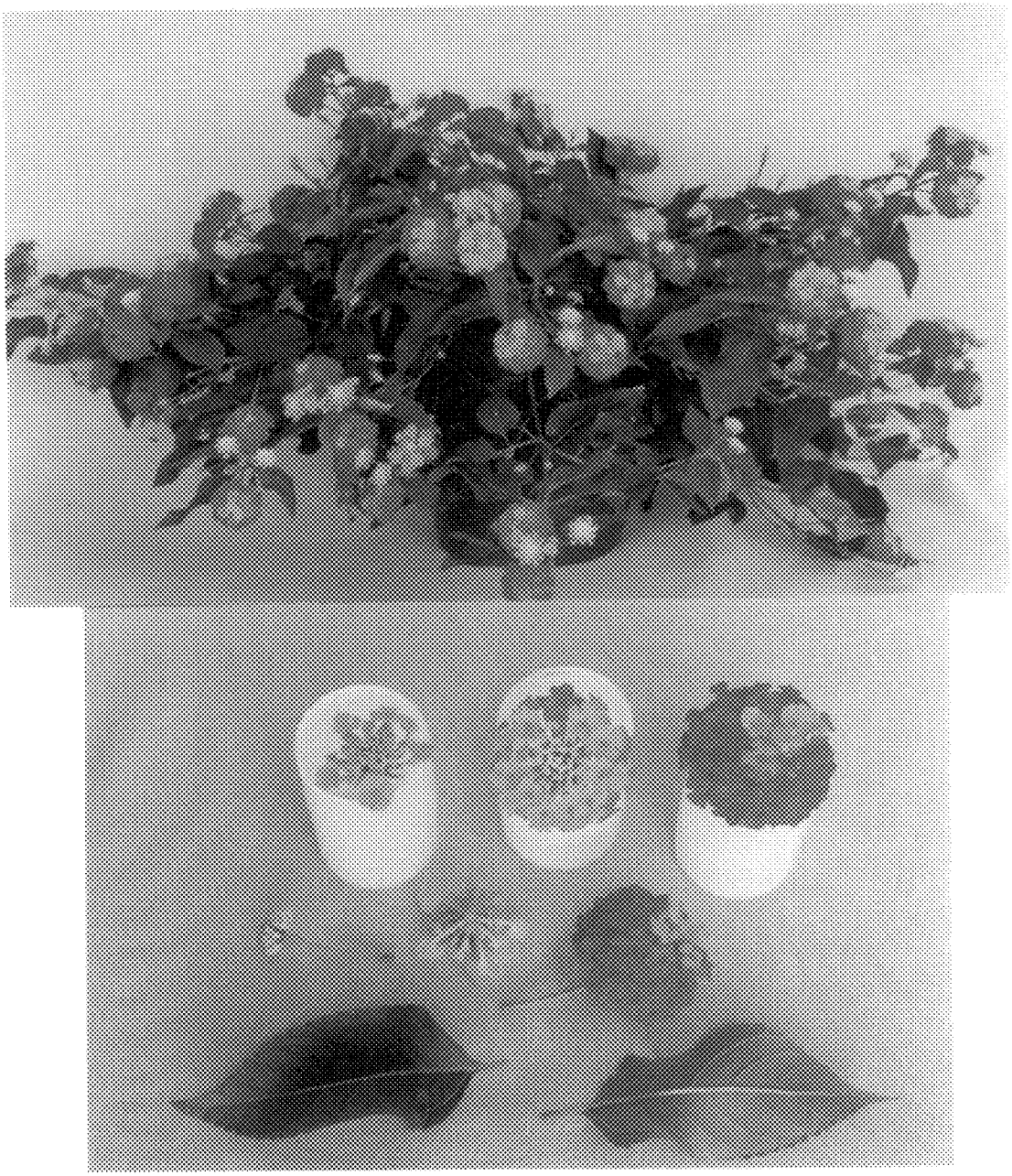

* * * * *